United States Patent [19]

Papay et al.

[11] 4,325,827

[45] Apr. 20, 1982

[54] FUEL AND LUBRICATING COMPOSITIONS CONTAINING N-HYDROXYMETHYL SUCCINIMIDES

[75] Inventors: Andrew G. Papay, Manchester; Joseph P. O'Brien, Kirkwood, both of Mo.

[73] Assignee: Edwin Cooper, Inc., St. Louis, Mo.

[21] Appl. No.: 228,129

[22] Filed: Jan. 26, 1981

Related U.S. Application Data

[63] Continuation-in-part of Ser. No. 60,280, Jul. 25, 1979, abandoned.

[51] Int. Cl.$^3$ .............................................. C10M 1/32
[52] U.S. Cl. ................................... 252/51.5 A; 44/63; 260/326.5 FM
[58] Field of Search ...................... 252/51.5 A; 44/63

[56] References Cited

U.S. PATENT DOCUMENTS

| | | | |
|---|---|---|---|
| 2,977,334 | 3/1961 | Zopf, Jr. et al. | 252/51.5 A X |
| 3,037,051 | 5/1962 | Stromberg | 252/51.5 A X |
| 3,219,666 | 11/1965 | Norman et al. | 252/51.5 A X |
| 3,458,444 | 7/1969 | Shepherd et al. | 252/51.5 A |
| 3,879,306 | 4/1975 | Kablaoui et al. | 252/51.5 A |
| 4,098,585 | 7/1978 | Vartanian et al. | 44/63 |
| 4,105,571 | 8/1978 | Shaub et al. | 252/51.5 A X |

FOREIGN PATENT DOCUMENTS

| | | | |
|---|---|---|---|
| 744377 | 10/1966 | Canada | 252/51.5 A |
| 1390948 | 9/1963 | France | 252/51.5 A |
| 478308 | 1/1938 | United Kingdom | 252/51.5 A |

*Primary Examiner*—Andrew Metz
*Attorney, Agent, or Firm*—Donald L. Johnson; John F. Sieberth; Joseph D. Odenweller

[57] ABSTRACT

Engine fuel economy is improved by adding a friction-reducing amount of a N-hydroxymethyl aliphatic hydrocarbyl succinimide to the engine crankcase oil or fuel.

8 Claims, No Drawings

FUEL AND LUBRICATING COMPOSITIONS CONTAINING N-HYDROXYMETHYL SUCCINIMIDES

This application is a continuation-in-part of application, Ser. No. 60,280, filed July 25, 1979 and now abandoned.

BACKGROUND OF THE INVENTION

In order to conserve energy, automobiles are not being engineered to give improved gasoline mileage compared to those in recent years. This effort is of great urgency as a result of Federal regulations recently enacted which compel auto manufacturers to achieve prescribed gasoline mileage. These regulations are to conserve crude oil. In an effort to achieve the required mileage, new cars are being down-sized and made much lighter. However, there are limits in this approach beyond which the cars will not accommodate a typical family.

Another way to improve fuel mileage is to reduce engine friction. The present invention is concerned with this latter approach.

Lubricating oil containing high molecular weight alkenyl succinimides of ethanolamine in which the alkenyl group contains at least 50 carbon atoms is disclosed in U.S. Pat. No. 3,219,666. They function as dispersants. Lubricating oil containing lower molecular weight alkenyl succinic esteramides of $C_{3-12}$ hydroxyalkylamine is reported in U.S. Pat. No. 3,037,051. They function as corrosion inhibitors. Automatic transmission fluid containing N-hydroxyalkyl succinamic acid is disclosed in U.S. Pat. No. 3,879,306.

SUMMARY

According to the present invention fuel efficient motor oil is provided which contains a friction-reducing amount of a N-hydroxymethyl $C_{12-36}$ aliphatic hydrocarbyl succinimide. The additives are also used in lquid hydrocarbon engine fuel.

DESCRIPTION OF THE PREFERRED EMBODIMENTS

A preferred embodiment of the invention is a lubricating oil composition formulated for use in the crankcase of an internal combustion engine said composition comprising a major amount of a lubricating oil and a minor friction-reducing amount of an oil-soluble N-hydroxymethyl aliphatic hydrocarbyl succinimide wherein said hydrocarbyl group contains about 12-36 carbon atoms.

These additives have the formula

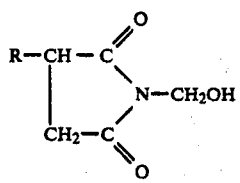

wherein R is an aliphatic hydrocarbon group containing about 12–36 carbon atoms. The group R can be any alkyl or alkenyl group. Examples of these are: n-dodecyl, n-dodecenyl, 2-ethyl dodecyl, n-tetradecenyl, n-hexadecyl, 2-butyl tetradecyl, n-octadecenyl, 2-ethykl octadecyl, 1-hexyl tetradecenyl, n-eicosenyl, n-docosyl, n-triacontenyl, 1-butyl triacontenyl, 2-hexyl triacontenyl, n-hexatriacontenyl.

In a highly preferred embodiment the aliphatic hydrocarbon group is bonded to the succinic group at a secondary carbon atom. These compounds have the formula:

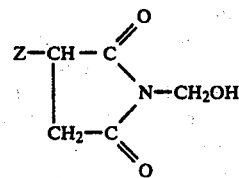

wherein Z is the group:

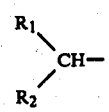

wherein $R_1$ and $R_2$ are independently selected from the group consisting of branched and straight chain hydrocarbon groups containing 1 to about 34 carbon atoms such that the total number of carbon numbers in $R_1$ and $R_2$ is about 11–35. Examples of these additives are:
N-hydroxymethyl 1-ethyltetradecyl succinimide
N-hydroxymethyl 1-methylpentadecenyl succinimide
N-hydroxymethyl 1,2-dimethyl octadecenyl succinamide
N-hydroxymethyl 1-methyl-3-ethyl dodecenyl succinimide
N-hydroxymethyl 1-decyl-2-methyl dotriacontyl succinimide In a more highly preferred embodiment $R_1$ and $R_2$ are straight chain aliphatic hydrocarbon groups. These additives have improved solubility in lubricating oil. Examples of these additives are:
N-hydroxymethyl 1-methylpentadecyl succinimide
N-hydroxymethyl 1-propyltridecenyl succinimide
N-hydroxymethyl 1-pentyltridecenyl succinimide
N-hydroxymethyl 1-tetradecyleicosenyl succinimide
N-hydroxymethyl 1-tridecylpentadecenyl succinimide The above highly preferred additives are preferably made from linear α-olefins containing about 12–36 carbon atoms by isomerizing the α-olefins to form a mixture of internal olefins, reacting this mixture of internal olefins with maleic acid, anhydride or ester forming an intermediate, reacting the intermediate with ammonia to form imide, and reacting this with formaldehyde to form the N-hydroxymethyl derivative.

Additives made from isomerized linear α-olefins have improved oil solubility compared with additives made with linear α-olefins.

Isomerization of the linear α-olefin can be carried out using conventional methods. One suitable method is to heat the linear α-olefin with an acidic catalyst. Especially useful acid catalysts are the sulfonated styrene-divinylbenzene copolymers. Such catalysts are commercially available and are conventionally used as cation exchange resins. In the present method they are used in their acid form. Typical resins are Amberlyst 15, XN-1005 and XN-1010 (registered trademarks) available from Rohm and Haas Company. Use of such resins for isomerizing linear α-olefins is described in U.S. Pat. No. 4,108,889, incorporated herein by reference.

The additives are readily made by reacting an appropriate $C_{12-36}$ aliphatic hydrocarbyl succinimide with formaldehyde. The following example illustrates the preparation of a typical additive.

EXAMPLE 1

This example shows the method for making hydrocarbyl succinimides.

In a reaction vessel was placed 185 grams of octadecenyl succinic anhydride. This was melted by heating to 60° C. and $NH_3$ was injected. An exothermic reaction proceeded raising the temperature to 160° C. with additional heating. After the reaction ceased the product was heated to 180° C. under 29" Hg vacuum to remove volatiles. The product was octadecenyl succinimide.

EXAMPLE 2

In a reaction vessel was placed 1 liter of heptane and 550 gms of octadecenyl succinimide. The mixture was heated to 70° C. with stirring and a mixture of 137 gms of 36% aqueous formaldehyde and 22 gms of sodium bicarbonate was added. This mixture was stirred at reflux for 4 hours. Then 300 ml of water was added and the mixture neutralized with hydrochloric acid. The aqueous layer was separated and removed, then 500 ml butanol was added to the organic layer and the mixture washed with hot water. The organic layer was separated and heptane, butanol and residual water distilled off leaving as the product N-hydroxymethyl-n-octadecenyl succinimide.

EXAMPLE 3

In a reaction vessel was placed 1000 grams of linear α-octadecene. To this was added 187 grams Amberlyst 15 (5% moisture). The mixture was stirred under nitrogen and heated at 120° C. for 3 hours. The isomerized product contained 3.6 wt % olefin dimer and the balance was internal $C_{18}$ olefin. The product was separated from the resin.

In a second reaction vessel was placed 504 grams of the above isomerized $C_{18}$ olefin and 300 ml heptane. The heptane was distilled out under vacuum to remove water. Then 2.4 grams of tri-(3,5-di-tert-butyl-4-hydroxybenzyl)mesitylene stabilizer was added. The mixture was heated under nitrogen to 225° C. Then 160 grams of molten maleic anhydride was slowly added over a 2.5-hour period. The mixture was stirred at 225° C. for two more hours and then unreacted maleic anhydride was distilled out by pulling vacuum to 30" Hg while holding the reaction mixture at 200° C. The product was principally secondary $C_{18}$ alkylene succinic anhydride.

In a separate reaction vessel was placed 532.5 grams of the above isomerized octadecenyl succinic anhydride. This was heated under nitrogen to 165° C. and then ammonia was injected causing the temperature to rise to 180° C. Ammonia injection was continued until exotherm stopped. The mixture was heated at 170° C. under vacuum to remove water yielding isomerized octadecenyl succinimide. This can then be reacted with formaldehyde as in Example 2 to form N-hydroxymethyl isomerized octadecenyl succinimide.

EXAMPLE 4

In a reaction vessel was placed 1005 grams of linear α-eicosene and 187 grams of Amberlyst 15 (5% moisture). The mixture was heated under nitrogen at 110°–125° C. for 6 hours. The product was internally unsaturated eicosene containing 3.3% eicosene dimer.

In a separate reaction vessel was placed 560 grams of the above isomerized eicosene and 200 ml heptane. The 3.1 grams of tri-(3,5-di-tert-butyl-4-hydroxybenzyl)-mesitylene stabilizer was added and the mixture heated to 210° C. Over a 2.5-hour period, 156.8 grams of maleic anhydride was added at about 225° C. Following this unreacted maleic anhydride was distilled out under vacuum at 210° C. leaving isomerized eicosenyl succinic anhydride.

In another reaction vessel was placed 570 grams of the above isomerized eicosenyl succinic anhydride. This was heated to 160° C. and ammonia injection started. The temperature rose to 175° C. Ammonia injection was continued at 175° C. until the temperature dropped. Then 30" Hg vacuum was slowly applied to distill out water and ammonia. Additional ammonia was injected to be sure no anhydride remained. There was no further reaction so this ammonia was stripped out at 30" Hg vacuum at 170° C. yielding isomerized eicosenyl succinimide. This can then be reacted with formaldehyde as in Example 2 to form N-hydroxymethyl isomerized eicosenyl succinimide.

EXAMPLE 5

In a reaction vessel was placed 1100 grams of linear $C_{16}$–$C_{18}$ α-olefin mixture. The olefin mixture was isomerized following the procedure in Example 4.

In a separate vessel was placed 485 grams (2 moles) of the above isomerized olefin. This was heated at 100° C. under 30" Hg vacuum to remove water. To it was then added 2.4 grams tri-(3,5-di-tert-butyl-4-hydroxybenzyl)-mesitylene. The mixture was heated under nitrogen to 225° C. and then 152 grams of molten maleic anhydride was added over a 3-hour period. The mixture was stirred 30 minutes at 225° C. and an additional 50 grams of maleic anhydride was added. This mixture was stirred 30 minutes at 225° C. following which unreacted maleic anhydride was distilled out at 200° C. under 30" Hg vacuum.

In a separate reaction vessel was placed 598 grams of the above isomerized $C_{16}$–$C_{18}$ alkenyl succinic anhydride. Ammonia injection was started at 140° C. raising the temperature to 145° C. Ammonia injection was continued at 130° C. until no further ammonia was adsorbed. The mixture was then heated to 180° C. to distill out water and ammonia yielding isomerized $C_{16}$–$C_{18}$ alkenyl succinimide. This can then be reacted with formaldehyde as in Example 2 to form N-hydroxymethyl isomerized $C_{16}$–$C_{18}$ olefin succinimide.

Other additives can be made following the above general procedure by substituting different hydrocarbyl succinimide.

The additives are added to lubricating oil in an amount which reduces the friction of an engine operating with the oil in the crankcase. A useful concentration is about 0.05–3 weight percent. A more preferred range is about 0.1–1.5 weight percent.

From the above it can be seen that the present invention provides an improved crankcase lubricating oil. Accordingly, an embodiment of the invention is an improved motor oil composition formulated for use as a crankcase lubricant in an internal combustion engine wherein the improvement comprises including in the crankcase oil an amount sufficient to reduce fuel consumption of the engine of the present additives.

In a highly preferred embodiment such improved motor oil also contains an ashless dispersant, a zinc dialkyldithiophosphonate and an alkaline earth metal salt of a petroleum sulfonic acid or an alkaryl sulfonic acid (e.g. alkylbenzene sulfonic acid).

The additives can be used in mineral oil or in synthetic oils of viscosity suitable for use in the crankcase of an internal combustion engine. Crankcase lubricating oils have a viscosity up to about 80 SUS at 210° F. According to the present invention the additives function to increase fuel economy when added to lubricating oil compositions formulated for use in the crankcase of internal combustion engines. Similar mileage benefits could be obtained in both spark ignited and diesel engines.

Crankcase lubricating oils of the present invention have a viscosity up to about SAE 40. Sometimes such motor oils are given a classification at both 0° and 210° F., such as SAE 10W 40 or SAE 5W 30.

Crankcase lubricants of the present invention can be further identified since they usually contain a zinc dihydrocarbyldithiophosphate in addition to the present additive. Likewise, these crankcase lubricants contain an alkaline earth metal sulfonate such as calcium petroleum sulfonate, calcium alkaryl sulfonate, magnesium petroleum sulfonate, magnesium alkaryl sulfonate, barium petroleum sulfonate, barium alkaryl sulfonate and the like.

Mineral oils include those of suitable viscosity refined from crude oil from all sources including Gulfcoast, midcontinent, Pennsylvania, California, Alaska and the like. Various standard refinery operations can be used in processing the mineral oil.

Synthetic oil includes both hydrocarbon synthetic oil and synthetic esters. Useful synthetic hydrocarbon oils include liquid polymers of $\alpha$-olefins having the proper viscosity. Especially useful are the hydrogenated liquid oligomers of $C_{6-12}$ $\alpha$-olefins such as $\alpha$-decene trimer. Likewise, alkylbenzenes of proper viscosity can be used, such as didodecylbenzene.

Useful synthetic esters include the esters of both monocarboxylic acid and polycarboxylic acid as well as monohydroxy alkanols and polyols. Typical examples are didodecyl adipate, trimethylol propane tripelargonate, pentaerythritol tetracaproate, di-(2-ethylhexyl)adipate, dilauryl sebacate and the like. Complex esters prepared from mixtures of mono- and dicarboxylic acid and mono- and polyhydroxyl alkanols can also be used.

Blends of mineral oil with synthetic oil are particularly useful. For example, blends of 10–25 weight percent hydrogenated $\alpha$-decene trimer with 75–90 weight percent 150 SUS (100° F.) mineral oil results in an excellent lubricant. Likewise, blends of about 10–25 weight percent di-(2-ethylhexyl)adipate with mineral oil of proper viscosity results in a superior lubricating oil. Also blends of synthetic hydrocarbon oil with synthetic esters can be used. Blends of mineral oil with synthetic oil are especially useful when preparing low viscosity oil (e.g. SAE 5W 20) since they permit these low viscosities without contributing excessive volatility.

The more preferred lubricating oil composition includes zinc dihydrocarbyldithiophosphate (ZDDP) in combination with the present additives. Both zinc dialkyldithiophosphates and zinc dialkaryldithiophosphates as well as mixed alkyl-aryl ZDDP are useful. A typical alkyl-type ZDDP contains a mixture of isobutyl and isoamyl groups. Zinc dinonylphenyldithiophosphate is a typical aryl-type ZDDP. Good results are achieved using sufficient ZDDP to provide about 0.01–0.5 weight percent zinc. A preferred concentration supplies about 0.05–0.3 weight percent zinc.

Another additive used in the oil compositions are the alkaline earth metal petroleum sulfonates or alkaline earth metal alkaryl sulfonates. Examples of these are calcium petroleum sulfonates, magnesium petroleum sulfonates, barium alkaryl sulfonates, calcium alkaryl sulfonates or magnesium alkaryl sulfonates. Both the neutral and the overbased sulfonates having base numbers up to about 400 can be beneficially used. These are used in an amount to provide about 0.05–1.5 weight percent alkaline earth metal and more preferably about 0.1–1.0 weight percent. In a most preferred embodiment the lubricating oil composition contains a calcium petroleum sulfonate or alkaryl (e.g. alkylbenzene) sulfonate.

Viscosity index improvers can be included such as the polyalkylmethacrylate type or the ethylene-propylene copolymer type. Likewise, styrene-diene VI improvers or styrene-acrylate copolymers can be used. Alkaline earth metal salts of phosphosulfurized polyisobutylene are useful.

Most preferred crankcase oils also contain an ashless dispersant such as the polyolefin-substituted succinamides and succinimides of polyethylene polyamines such as tetraethylenepentamine. The polyolefin succinic substituent is preferably a polyisobutene group having a molecular weight of from about 800 to 5,000. Such ashless dispersants are more fully described in U.S. Pat. No. 3,172,892 and U.S. Pat. No. 3,219,666 incorporated herein by reference.

Another useful class of ashless dispersants are the polyolefin succinic esters of mono- and polyhydroxy alcohols containing 1 to about 40 carbon atoms. Such dispersants are described in U.S. Pat. Nos. 3,381,022 and 3,522,179.

Likewise, mixed ester/amides of polyolefin substituted succinic acid made using alkanols, amines and/or aminoalkanols represent a useful class of ashless dispersants.

The succinic amide, imide and/or ester type ashless dispersants may be boronated by reaction with a boron compound such as boric acid. Likewise, the succinic amide, imide, and/or ester may be oxyalkylated by reaction with an alkylene oxide such as ethylene oxide or propylene oxide.

Other useful ashless dispersants include the Mannich condensation products of polyolefin-substituted phenols, formaldehyde and polyethylene polyamine. Preferably, the polyolefin phenol is a polyisobutylene-substituted phenol in which the polyisobutylene group has a molecular weight of from about 800 to 5,000. The preferred polyethylene polyamine is tetraethylene pentamine. Such Mannich ashless dispersants are more fully described in U.S. Pat. Nos. 3,368,972; 3,413,347; 3,442,808; 3,448,047; 3,539,633; 3,591,598; 3,600,372; 3,634,515; 3,697,574; 3,703,536; 3,704,308; 3,725,480; 3,726,882; 3,736,357; 3,751,365; 3,756,953; 3,792,202; 3,798,165; 3,798,247 and 3,803,039.

The above Mannich dispersants can be reacted with boric acid to form boronated dispersants having improved corrosion properties.

Superior results are obtained by using the present additives in crankcase lubricating oil in combination with a phosphonate additive. Preferred phosphonates are the di-$C_{1-4}$ alkyl $C_{12-36}$ alkyl or alkenyl phosphonates. These compounds have the structure:

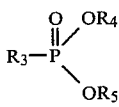

wherein $R_3$ is an aliphatic hydrocarbon group containing about 12–36 carbon atoms and $R_4$ and $R_5$ are independently selected from lower alkyl groups containing about 1–4 carbon atoms. Representative examples of these coadditives are:
dimethyl octadecylphosphonate
dimethyl octadecenylphosphonate
diethyl 2-ethyldecylphosphonate
ethyl propyl 1-butylhexadecylphosphonate
methyl ethyl octadecylphosphonate
methyl butyl eicosylphosphonate
dimethyl hexatriacontylphosphonate When using the phosphonate coadditive only a small amount is required. A useful range is about 0.005–0.75 weight percent based on the formulated oil. A more preferred amount is about 0.05–0.5 weight percent.

In commercial practice a preferred way to add the present additives to lubricating oil is in the form of an additive package. These are concentrates dissolved in oil which when added to a base oil will provide an effective concentration of the present additive and other known additives. For example, if the desired use level is 0.2 wt % and the final formulated oil is made by adding 10 parts of additive package to 90 parts of base lubricating oil, then the additive pack will contain 2.0 wt % of the present additive.

In addition to the present additives, such additive packages usually contain an ashless dispersant such as those previously discussed. In addition, the additive package may contain the phosphonate coadditive, a zinc dialkyldithiophosphate, an alkaline earth metal hydrocarbonsulfonate (either neutral or overbased), an alkaline earth metal phenate (either neutral or overbased), or similar sulfur-bridged phenates, an antioxidant such as 4,4'-methylenebis-(2,6-di-tert-butylphenol) or N-octylphenyl-α-naphthylamine, a phosphosulfurized terpene or olefin such as phosphosulfurized polyisobutylene (mol wt 1000) or alkaline earth metal salts of such phosphosulfurized olefin, a viscosity index improver such as a polyalkylmethacrylate, an ethylene/propylene copolymer, an ethylene/propylene/non-conjugated diene terpolymer, a styrene/conjugated diene copolymer, a styrene/acrylate copolymer and the like may be included in the package or may be added separately to the oil.

The following formulation illustrates a typical additive package of this invention. Parts are by weight.

| | |
|---|---|
| N-hydroxymethyloctadecenyl succinimide | 1.2–12 parts |
| polyisobutenyl (mol wt 950) succinimide of tetraethylenepentamine | 2.4–120 parts |
| zinc dialkyldithiophosphate (10% Zn) | 6–24 parts |
| calcium alkyl benzene sulfonate (TBN 300) | 12–60 parts |
| dimethyloctadecylphosphonate | 1.2–12 parts |
| Acryloid 702[1] | 60–180 parts |
| neutral 100 SUS mineral oil | 5–50 parts |

[1]registered trademark for Rohm and Haas Company brand of polymethacrylate VI improver The friction reducing additives of this invention are also useful in fuel compositions. Fuel injected or inducted into a combustion chamber wets the walls of the cylinder. Fuels containing a small amount of the present additive reduce the friction due to the piston rings sliding against the cylinder wall.

The additives can be used in both diesel fuel and gasoline used to operate internal combustion engines. Fuels containing about 0.001–0.25 weight percent of the N-hydroxymethyl hydrocarbylsuccinimide can be used.

Fuels used with the invention can contain any of the additives conventionally added to such fuels. In the case of gasoline it can include dyes, antioxidants, detergents, antiknocks (e.g. tetraethyllead, methylcyclopentadienylmanganese tricarbonyl, rare earth metal chelates, methyl tertbutylether and the like). In the case of diesel fuels the compositions can include pour point depressants, detergents, ignition improvers (e.g. hexylnitrate) and the like.

Tests were conducted which demonstrated the friction reducing properties of the present invention.

LFW-1 Test

In this test a metal cylinder is rotated around its axis 45° in one direction and then 45° in the opposite direction at a rate of 120 cycles per minute. A metal block curved to conform to the circular contour of the cylinder presses at a fixed load against the periphery of the cylinder. Test lubricant is applied to the rubbing surface between the cylinder and the block. Torque transmitted to the block from the oscillating cylinder is measured. The greater the torque the greater the friction. Results are given in terms of "percent improvement" which is the percent reduction in torque compared to that obtained with the test oil without the test additive.

SAE-2 Fly Wheel Test

In this test a heavy fly wheel is rotated at 1440 rpm. A series of 9 clutch plates are then brought to bear axially at a defined load against the fly wheel. The fly wheel is connected to the rotating plate. The static plates are connected to a device which measures rotational torque. The time from initially applying pressure through the clutch plate until the rotating plates stop rotating is measured. Also, the rotational torque measured at the static plates is plotted against time. Torque rises to a value referred to as "dynamic torque" and then rises to a maximum called "static torque" as the plates stop rotation. The clutch plates are immersed in test lubricant. A reduction in friction is indicated by (1) an increase in time required to stop the rotation of the moving plates and (2) a decrease in dynamic and static torque. Results are reported in percent time increase (percent improvement) and percent reduction in torque compared to that obtained using the same oil without the test additive.

The test oil is a fully formulated oil of SAE SE quality. Test results are given in the following table:

| | | SAE No. 2 % Improvement | | |
|---|---|---|---|---|
| Additive | LFW-1 % improvement | Time Increase | Dyn. | Static |
| N-hydroxymethyl octadecenyl succinimide (0.3%) | 11 | 8 | 12.5 | 21 |

| Additive | LFW-1 % improvement | SAE No. 2 % Improvement |  |  |
|---|---|---|---|---|
|  |  | Time Increase | Dyn. | Static |
| N-hydroxy-methyl octadecenyl succinimide + 0.2% dimethyl octadecyl phosphonate | 15 | 11 | 18 | 33 |

Further tests were carried out which demonstrated the friction-reducing properties of the additives. In these tests an engine with its cylinder head removed and with the test lubricating oil in its crankcase was brought to 1800 rpm by external drive. Crankcase oil was maintained at 63° C. The external drive was disconnected and the time to coast to a stop was measured. This was repeated several times with the base oil and then several times with the same oil containing one percent of test additive. The base oil was a typical commercial oil formulated for use in a crankcase. The following table shows the percent increase in coast-down time caused by the present additives.

| Additive | Percent Increase |
|---|---|
| N-hydroxymethyl octadecenyl succinimide (1%) | 9% |

The results show that the additives of this invention provide a significant reduction in friction.

Still further, tests were carried out in a 1978 sedan with a V-8 engine. The test oil was a formulated SE 10W 40 motor oil containing 0.6 wt % N-hydroxymethyl octadecenyl succinimide and 0.2 wt % dimethyl octadecylphosphonate. The test was the SAE J 1082A Fuel Economy Test. In this test the vehicle is driven over an urban driving cycle, a suburban driving cycle and an interstate driving cycle. Fuel consumption is measured and compared against the baseline of the car on each cycle without the test additives. The results were as follows:

| Percent Improvement In Fuel Economy | | |
|---|---|---|
| Urban Cycle | Suburban Cycle | Interstate Cycle |
| 5.3, 6.5 | 2.5 | 2.1 |

The results showed that the additives were effective under all conditions in improving fuel economy and were especially effective in urban driving.

The LFW-1 test was also conducted on products made by reacting octadecenyl succinic anhydride with N-hydroxyethylamine to demonstrate the unexpected superiority of the present N-hydroxymethyl derivatives. These tests were conducted at 60 cycles per minute instead of 120 cycles per minute. The first N-hydroxyethyl derivative was made in a manner similar to that described in Knapp Canadian 744, 377 by heating 126 grams of octadecenyl succinic anhydride to 130° C. and adding 61.6 grams of ethanolamine dropwise. The mixture was heated to 160° C. and stirred for two hours, at which time volatiles were removed at 165° C. under 30 inches Hg vacuum.

A series of the above described LFW-1 test was conducted in which the N-hydroxymethyl and N-hydroxyethyl derivatives were bracketed between non-additive reference tests. The following table gives the results in terms of percent improvement compared to the bracketed reference test.

| Additive | Percent Improvement |
|---|---|
| Reference | — |
| N-hydroxymethyl | 13.9 |
| Reference | — |
| Reference | — |
| N-hydroxyethyl | 10.1 |
| Reference | — |
| N-hydroxyethyl | 9.9 |
| Reference | — |
| Reference | — |
| N-hydroxymethyl | 14.4 |
| Reference | — |

The friction reduction with the N-hydroxymethyl derivative was about 40 percent greater than that obtained with the N-hydroxyethyl derivative.

Another N-hydroxyethylamine/octadecenyl succinic anhydride reaction product similar to that described in Kablaoui et al, U.S. Pat. No. 3,879,306 was made by adding 15.25 grams (0.25 moles) of ethanolamine to a mixture of 87.5 grams (0.25 moles) of octadecenyl succinic anhydride in 99.7 grams of mineral oil at 40° C. over a 20 minute period. The mixture was heated to 120° C. for 30 minutes. The product had a total acid number (TAN) of 47.8. This product was split into two equal parts and one of these parts was heated at 120° C. for an additional 30 minutes. This gave a TAN of 26.5. A blend of 40 grams of the 47.8 TAN product and 60 grams of the 26.5 TAN product was made to obtain a blend of 35 TAN product. TAN of 35 corresponds to a product which contains N-hydroxyethyloctadecenyl succinamic acid and N-hydroxyethyloctadecenyl succinimide at a 1:1 weight ratio. This product was 50 weight percent active, the balance being mineral oil.

The above N-hydroxyethyl product was compared to the N-hydroxymethyl product of this invention using the previously described LFW-1 friction test at 60 cycles per minute. Each test was bracketed by non-additive reference oils, and the results reported in terms percent improvement over the bracketed reference oils. The following table gives the results:

| Additive | Percent Improvement |
|---|---|
| Reference | — |
| N-hydroxyethyl[1] | 4.8 |
| Reference | — |
| N-hydroxyethyl[1] | 5.4 |
| Reference | — |
| N-hydroxymethyl[2] | 8.1 |
| Reference | — |
| N-hydroxymethyl[2] | 8.1 |
| Reference | — |
| N-hydroxyethyl[3] | 6.6 |
| Reference | — |
| N-hydroxyethyl[3] | 7.4 |
| Reference | — |
| N-hydroxymethyl[4] | 10.4 |
| Reference | — |
| N-hydroxymethyl[4] | 11.2 |
| Reference | — |

[1]Concentration 0.3 wt. percent of 50 percent active product
[2]Concentration 0.15 wt. percent of 100 percent active product
[3]Concentration 0.6 wt. percent 50 percent active product
[4]Concentration 0.3 wt. percent 100 percent active product The above results show that when compared at the same 0.15 weight percent basis, the friction reduction averages as follows:

N-hydroxymethyl: 8.1 percent
N-hydroxyethyl: 5.1 percent

When compared at the same 0.3 weight percent basis, the products show the following average improvement:

N-hydroxymethyl: 10.8 percent
N-hydroxyethyl: 7.0 percent

It is interesting to note that the N-hydroxymethyloctadecenyl succinimide of this invention is more effective (8.1 percent improvement) at a concentration of 0.15 weight percent than the corresponding N-hydroxyethyloctadecenyl succinimide-succinamic product (7.0 percent improvement) at twice the concentration (0.3 weight percent).

We claim:

1. A lubricating oil composition formulated for use in the crankcase of an internal combustion engine said composition comprising a major amount of a lubricating oil and a minor friction-reducing amount of an oil-soluble N-hydroxymethyl aliphatic hydrocarbyl succinimide wherein said hydrocarbyl group contains about 12–36 carbon atoms said succinimide being made by reacting ammonia with an aliphatic $C_{12-36}$ hydrocarbyl succinic anhydride to form the corresponding succinimide and subsequently reacting the succinimide with formaldehyde to form said N-hydroxymethyl aliphatic hydrocarbyl succinimide.

2. A lubricating oil composition of claim 1 wherein said lubricating oil is selected from mineral oil, synthetic hydrocarbon oils and mixtures thereof.

3. A lubricating oil composition of claim 1 or 2 wherein said hydrocarbyl is an alkenyl group containing about 12–24 carbon atoms.

4. A lubricating oil composition of claim 1 or 2 wherein said hydrocarbyl is octadecenyl.

5. An additive concentrate adapted for addition to lubricating oil for use in the crankcase of an internal combustion engine said concentrate containing an oil soluble N-hydroxymethyl aliphatic hydrocarbyl succinimide said succinimide being made by reacting ammonia with an aliphatic $C_{12-36}$ hydrocarbyl succinic anhydride to form the corresponding succinimide and subsequently reacting the succinimide with formaldehyde to form said N-hydroxy-methyl aliphatic hydrocarbyl succinimide.

6. An additive concentrate of claim 5 wherein said hydrocarbyl is an alkenyl group containing about 12–24 carbon atoms.

7. An additive concentrate of claim 6 wherein said alkenyl group is octadecenyl.

8. Liquid hydrocarbon fuel adapted for use in an internal combustion engine containing a friction-reducing amount of a fuel-soluble N-hydroxymethyl aliphatic hydrocarbyl succinimide wherein said hydrocarbyl contains about 12–16 carbon atoms said succinimide being made by reacting ammonia with an aliphatic $C_{12-36}$ hydrocarbyl succinic anhydride to form the corresponding succinimide and subsequently reacting the succinimide with formaldehyde to form said N-hydroxymethyl aliphatic hydrocarbyl succinimide.

* * * * *